(12) United States Patent
Stegemann et al.

(10) Patent No.: US 10,610,490 B2
(45) Date of Patent: Apr. 7, 2020

(54) SEPARABLE CAPSULE FOR SPRINKLING APPLICATIONS

(71) Applicant: Capsugel Belgium NV, Bornem (BE)

(72) Inventors: Sven Stegemann, Aachen (DE); Stefaan Jaak Vanquickenborne, Rijmenam (BE); Hilde Buydts, Antwerp (BE)

(73) Assignee: Capsugel Belgium NV, Bornem (BE)

(*) Notice: Subject to any disclaimer, the term of this patent is extended or adjusted under 35 U.S.C. 154(b) by 0 days.

(21) Appl. No.: 15/595,848

(22) Filed: May 15, 2017

(65) Prior Publication Data

US 2017/0333358 A1  Nov. 23, 2017

(30) Foreign Application Priority Data

May 18, 2016 (EP) .................................... 16170066

(51) Int. Cl.
| | |
|---|---|
| *A61J 3/07* | (2006.01) |
| *A61K 9/00* | (2006.01) |
| *A61K 9/48* | (2006.01) |
| *A61J 1/00* | (2006.01) |

(52) U.S. Cl.
CPC .............. *A61K 9/4808* (2013.01); *A61J 1/00* (2013.01); *A61J 3/071* (2013.01); *A61K 9/0056* (2013.01); *A61K 9/4866* (2013.01); *A61J 2205/00* (2013.01); *A61J 2205/40* (2013.01); *A61J 2205/50* (2013.01)

(58) Field of Classification Search
None
See application file for complete search history.

(56) References Cited

U.S. PATENT DOCUMENTS

| | | | |
|---|---|---|---|
| 3,702,653 A | 11/1972 | Mottin et al. | |
| 5,624,681 A | 4/1997 | Tanner et al. | |
| 2002/0144383 A1* | 10/2002 | Spence | A61G 17/00 27/35 |
| 2016/0022593 A1* | 1/2016 | Buydts | A61J 3/072 424/454 |
| 2016/0074326 A1 | 3/2016 | Rariy et al. | |

FOREIGN PATENT DOCUMENTS

| | | |
|---|---|---|
| EP | 0951835 | 10/1999 |
| EP | 0946637 B1 | 1/2001 |
| EP | 1204699 B1 | 6/2005 |
| EP | 1301178 B1 | 1/2007 |
| EP | 1057862 B1 | 6/2007 |
| EP | 2078042 A1 | 7/2009 |
| EP | 2480218 A1 | 8/2012 |
| EP | 2994114 A1 | 3/2016 |
| EP | 324600 | 11/2017 |
| GB | 2356842 | 6/2001 |
| WO | WO2012/095746 A2 | 7/2012 |
| WO | WO2014/181200 | 11/2014 |
| WO | WO-2014181200 A1 * | 11/2014 .............. A61J 3/072 |

OTHER PUBLICATIONS

Extended Search Report for European Patent Publication No. 16170066.1 (dated Nov. 18, 2016).
Office Action for European Application No. 16170066.1 (dated Jan. 7, 2019).
Office Action for European Application No. 16170066.1 (dated Aug. 2, 2019).

* cited by examiner

*Primary Examiner* — Susan T Tran
(74) *Attorney, Agent, or Firm* — Klarquist Sparkman, LLP

(57) ABSTRACT

A comestible dosage form article, in the form of a hard capsule, for administration to a target subject, the dosage form comprising at least one body and at least one cap telescopically engageable with the body, the cap and the body being separable such to allow dispensing of a contents therefrom. The capsule comprising a sensory trigger over at least a portion of the outer surface of the capsule arranged to provide a visual, taste, and/or tactile deterrence to ingestion thereof.

16 Claims, 6 Drawing Sheets

SEPARABLE CAPSULE FOR SPRINKLING APPLICATIONS

CROSS REFERENCE TO RELATED APPLICATION

This application claims the benefit of European Patent Application No. 16170066.1, filed May 18, 2016, which is hereby incorporated by reference.

FIELD

The present disclosure relates to ingestible dosage form articles, preferably multi-part capsules, suitable for the delivery of one or more drugs. More particularly, the dosage form articles are suitable for ingestion by a subject, preferably the subject being selected from humans or animals.

In particular, hard capsules described herein are designed and intended for deterring oral administration thereof, preferably for directly mixing the content therein into a comestible food product, and/or to improve ease of opening thereof typically compared to a capsule free of the sensory trigger described herein.

BACKGROUND

Capsule technology continues to be subject to development and improvements. In its basic form, standard containers for pharmaceuticals or other powdered, granular or liquid substances (generally referred to as telescope-type, multi-part, or two-piece capsules) include a tubular-shaped and/or cylindrically-shaped first part, namely a cap part, which is closed on one end and open on the other opposite end. A tightly fitting second part of similar shape, namely the body part, is of smaller diameter than the cap part and is typically telescopically engaged therein to form the overall dosage form or two-piece capsule. Similar capsule technology may be used to generate multi-compartment capsules.

The vast majority of capsules are intended for oral delivery, and may comprise single or multi-compartment capsules for delivery of one or more active materials by ingestion of such capsules via the oral route. These include capsules for delayed and target release in specific delivery areas of the gastro intestinal tract typically by improving the acid resistance of the shells of the capsules. A number of ways for improving acid resistance of capsules have been described in the literature.

Examples of single compartment hard capsules are ones as described in EP0861061B1 and sold by Capsugel® under the brand Coni-Snap®. Such can be made of gelatin or specialty polymers like HPMC (like Vcaps®, Vcaps® Plus, DRcaps®) or pullulan (like Plantcaps®), the compositions further being described and exemplified in EP0946637B1, EP105786281, EP2078042A1, EP2480218A1, EP120469981, and WO2012/095746A2 respectively.

Examples of multi-compartment capsules include the capsule-in-capsule executions described in EP1301178B1, wherein an inner capsule containing a substance is contained within an outer (larger) capsule further comprising a substance which can be the same or different from the substance contained in the inner capsule.

A different form of delivery, to classic oral administration, is that of sprinkle applications (particularly suitable for some delivery products or geriatric/pediatric subjects with swallowing difficulties). In such case the capsule is designed to be more easily openable compared to dosage forms designed for oral delivery by reducing the locking force generated by the engaged cap and body parts of the capsule, an example is described in EP2994114A1.

In this latter form of delivery in particular, it is desirable to on the one hand ensure that such capsules are not accidentally swallowed, and on the other hand ensure that opening of the capsule is further improved whilst maintaining an attractive overall aesthetic impact in the eyes of a subject.

A need therefore exists to develop a capsule and methods of making that provide this additional functionality particularly desirable in the sprinkle-type form of delivery.

SUMMARY

A first aspect of the present disclosure relates to a dosage form article for sprinkle administration to a target subject, the dosage form comprising: at least one body and at least one cap telescopically engageable with said body wherein said cap and said body are separable such to allow dispensing of a contents therefrom and wherein said capsule comprises a sensory trigger over at least a portion of the outer surface of said capsule arranged to provide a visual, taste, and/or tactile deterrence to ingestion of said hard capsule.

A further aspect of the present disclosure relates to a method of making a dosage form comprising the steps of: providing a capsule body and cap; telescopically joining the body and cap to form a hard capsule; applying a sensory trigger over at least a portion of the outer surface of said capsule, said sensory trigger arranged to provide a visual, taste, and/or tactile deterrence to ingestion of said hard capsule.

A further aspect of the present disclosure relates to a use of a hard capsule comprising a sensory trigger for deterring oral administration thereof, preferably for directly mixing the content therein into a comestible food product, and/or to improve ease of opening thereof compared to a capsule free of the sensory trigger.

DETAILED DESCRIPTION

Figure 1:
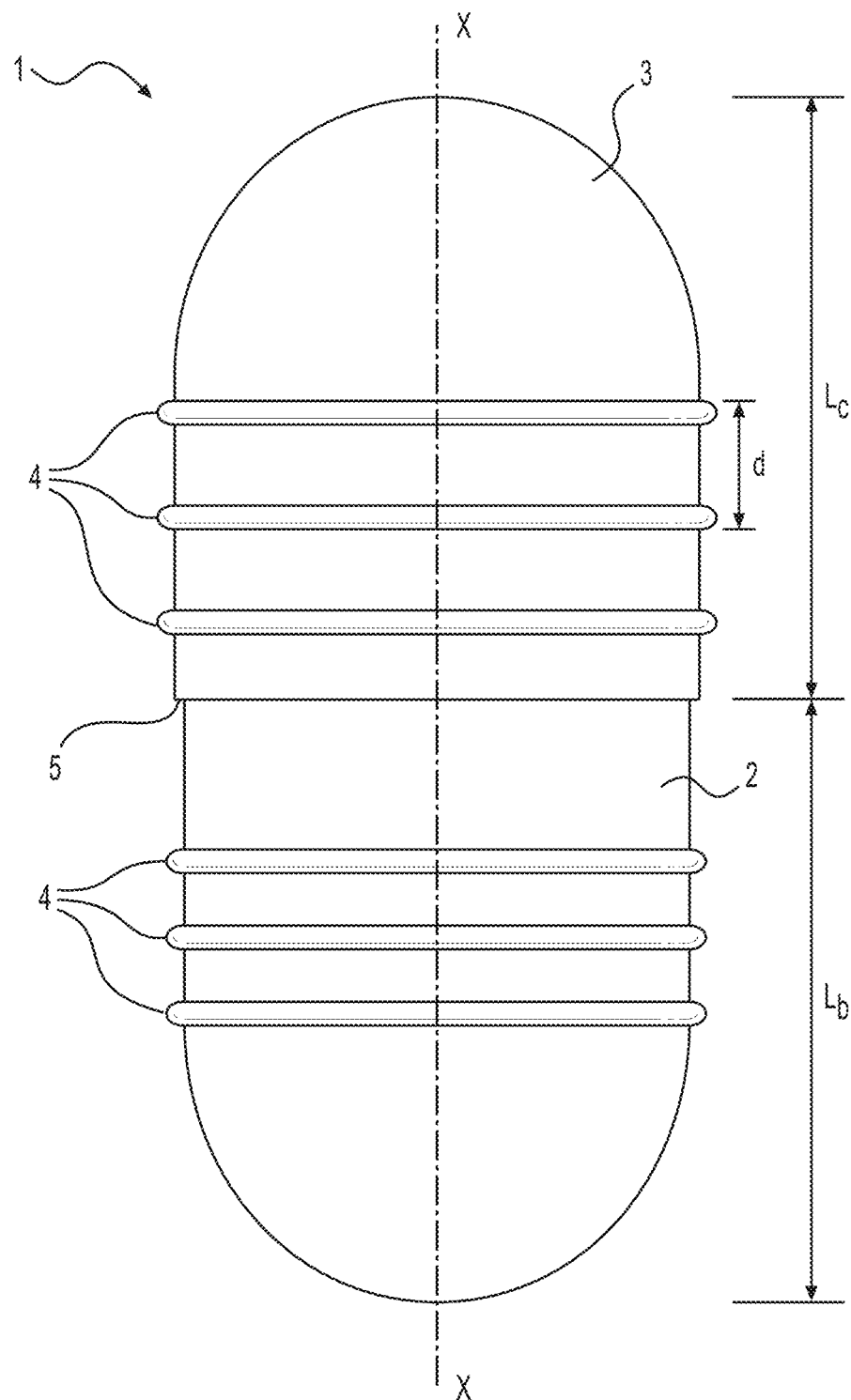
FIG. 1 is a schematic illustration of a capsule according to an embodiment of the disclosure.
Figure 2:
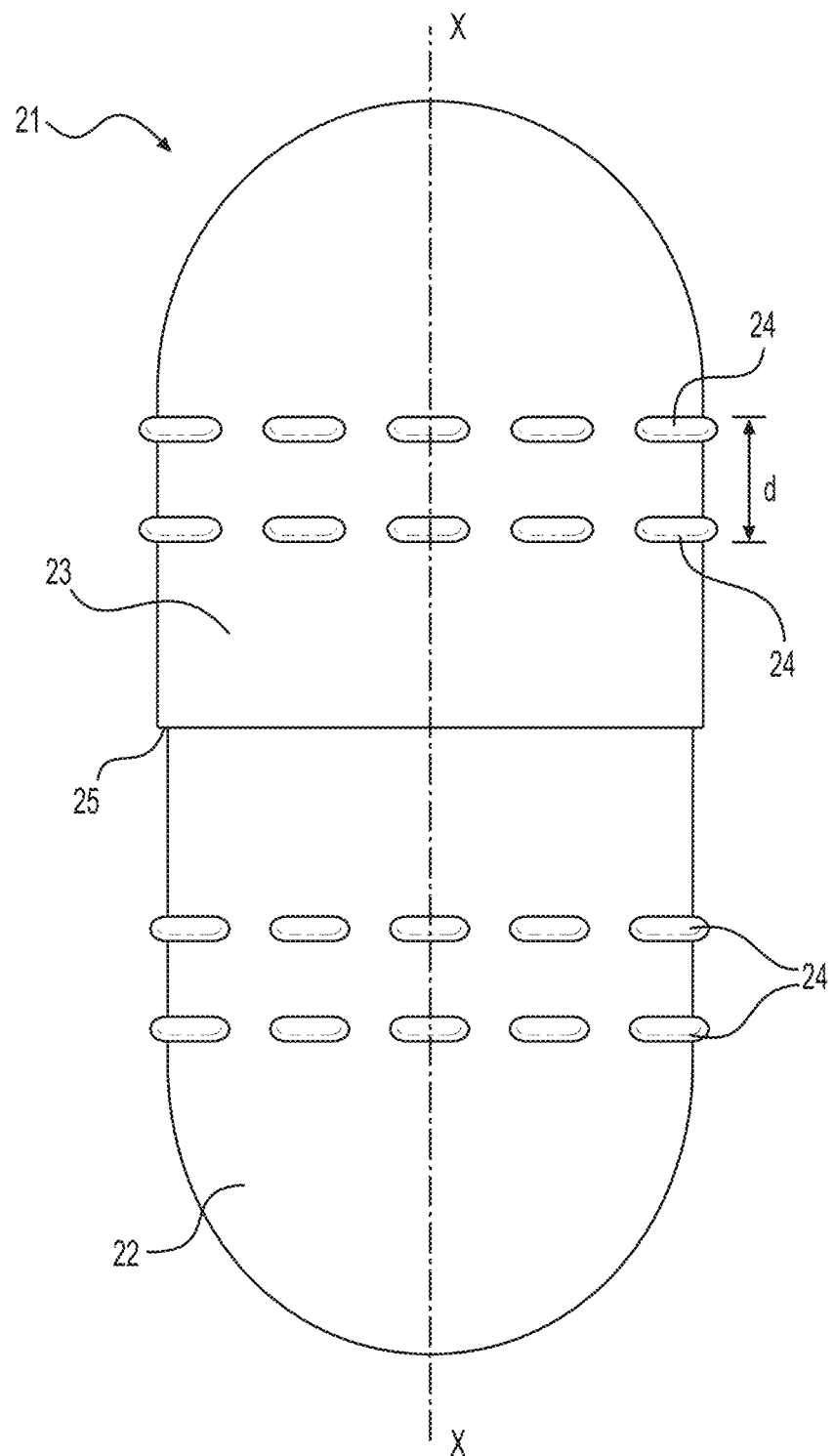
FIG. 2 is a schematic illustration of a capsule according to an embodiment of the disclosure.
Figure 3:
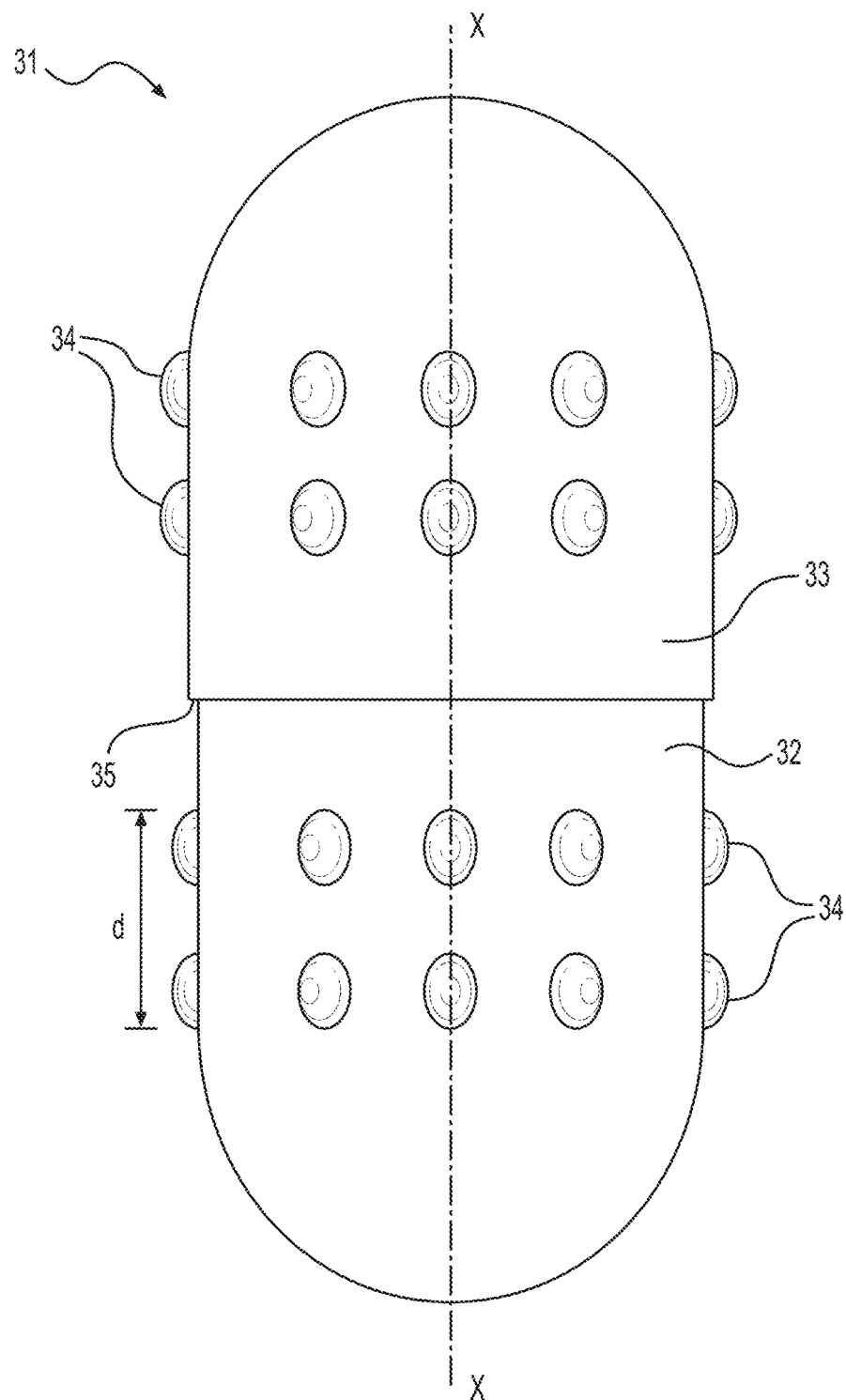
FIG. 3 is a schematic illustration of a capsule according to an embodiment of the disclosure.

By the term "a" and/or "an" when describing a particular element, it is intended "at least one" of that particular element.

By the term "medicament", it is intended a "drug" or the like comprising one or more compounds providing one or more curative benefits to a subject, the terms "medicament" and "drug" may be used interchangeably herein.

By the term "hard shell" or "hard capsule shell", it is intended a shell that is deformable, but which returns to its un-deformed shape upon the removal of a deforming force. Typically such shells comprise, for example, less than 25%, preferably less than 20%, more preferably from 0% to 14%, even more preferably from greater than 0% to less than 14%, water by weight.

Various embodiments will now be described to provide an overall understanding of the principles of the structure, function, manufacture, and use of dosage form articles and methods disclosed herein. One or more examples of these embodiments are illustrated in the accompanying figures. Those of ordinary skill in the art will immediately understand that features described or illustrated in connection with one example embodiment can be combined with the features of other example embodiments without generalization from the present disclosure.

Dosage Form Articles

Referring to the figures, the disclosure herein relates to a comestible hard capsule 1, 21, 31, 41, 51 for sprinkle applications comprising at least one body 2, 22, 32, 42, 52 and at least one cap 3, 23, 33, 43, 53 telescopically engageable with said body 2, 22, 32, 42, 52 wherein said cap 3, 23, 33, 43, 53 and said body 2, 22, 32, 42, 52 are separable such to allow dispensing of a contents therefrom and wherein said capsule 1, 21, 31, 41, 51 comprises a sensory trigger 4, 24, 34, 44, 54 over at least a portion of the outer surface of said capsule 1, 21, 31, 41, 51 arranged to provide a visual, taste, and/or tactile deterrence to ingestion of said hard capsule 1, 21, 31, 41, 51.

In an embodiment, the sensory trigger 4, 24, 34, 44, 54 is localized over only a portion of the cap 3, 23, 33, 43, 53 and/or body 2, 22, 32, 42, 52 of the capsule 1, 21, 31, 41, 51 (i.e., is not a surface coating over the entire capsule). An advantage of this embodiment is to better differentiate the visual appearance compared to classic hard capsules for oral administration and provide a more intuitive signal to the subject.

In an embodiment, the sensory trigger 4, 24, 34, 44, 54 comprises one or more protrusions, preferably at least 2, more preferably at least 4, and typically in the form of continuous rings along the circumference of the cap 3, 23, 33, 43, 53 and/or body 2, 22, 32, 42, 52 generally each said ring disposed substantially parallel to each other and at a distance d separating each said ring in a direction parallel to a capsule centerline X. An advantage of such arrangement is to provide tactile and visual deterrence as well as improving ease of opening of the capsule.

In an alternative embodiment, the sensory trigger 4, 24, 34, 44, 54 comprises one or more protrusions, preferably at least 2, more preferably at least 4, even more preferably from 5 to 16, and typically in the form of discontinuous rings along the circumference of the cap 3, 23, 33, 43, 53 and/or body 2, 22, 32, 42, 52 generally each said ring being disposed substantially parallel to each other and at a distance d separating each said ring in a direction parallel to a capsule centerline X, and wherein each said discontinuous ring is formed by a plurality of protrusions and/or recesses arranged in series.

Figure 4:
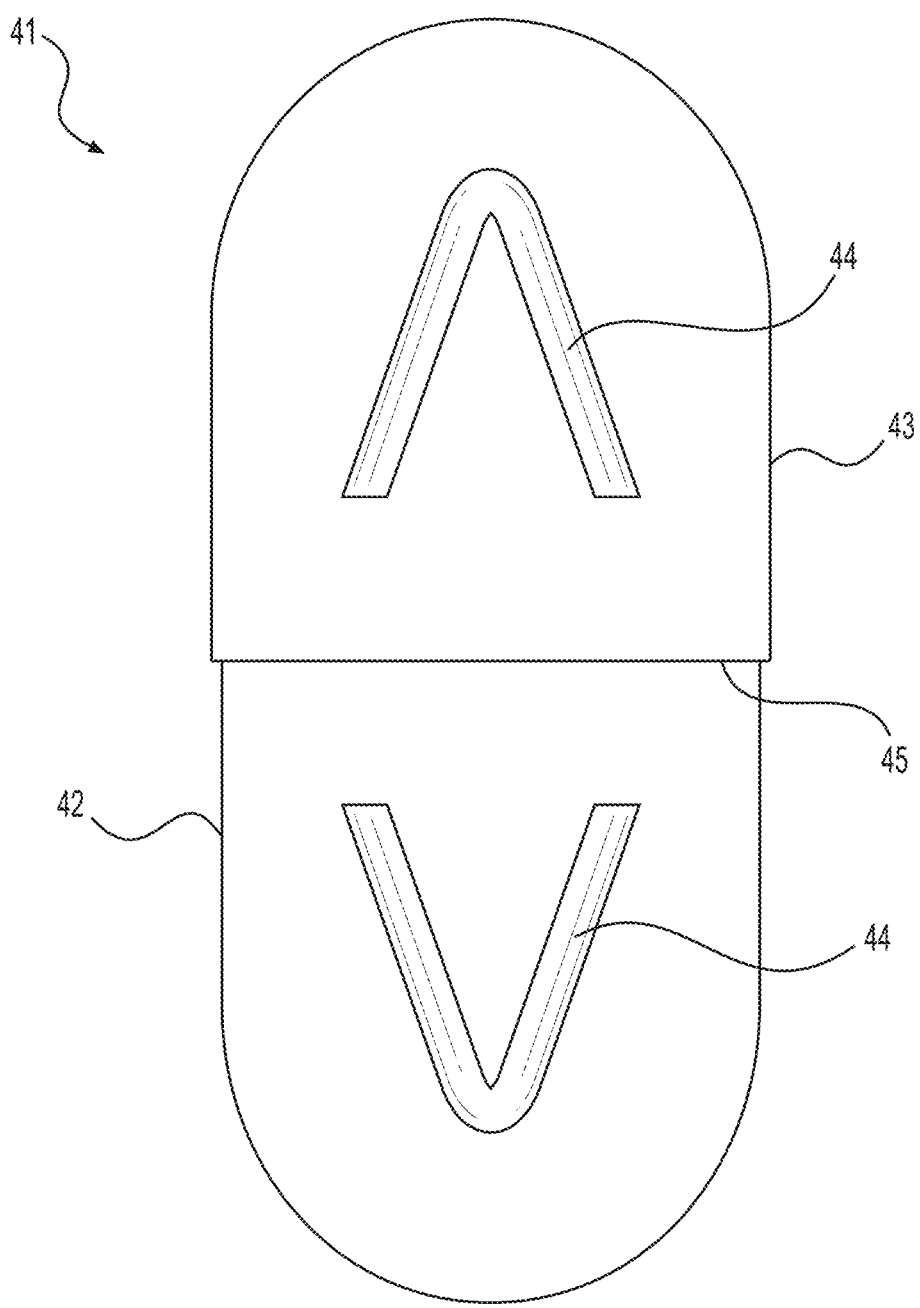
FIG. 4 is a schematic illustration of a capsule according to an embodiment of the disclosure.
Figure 5:
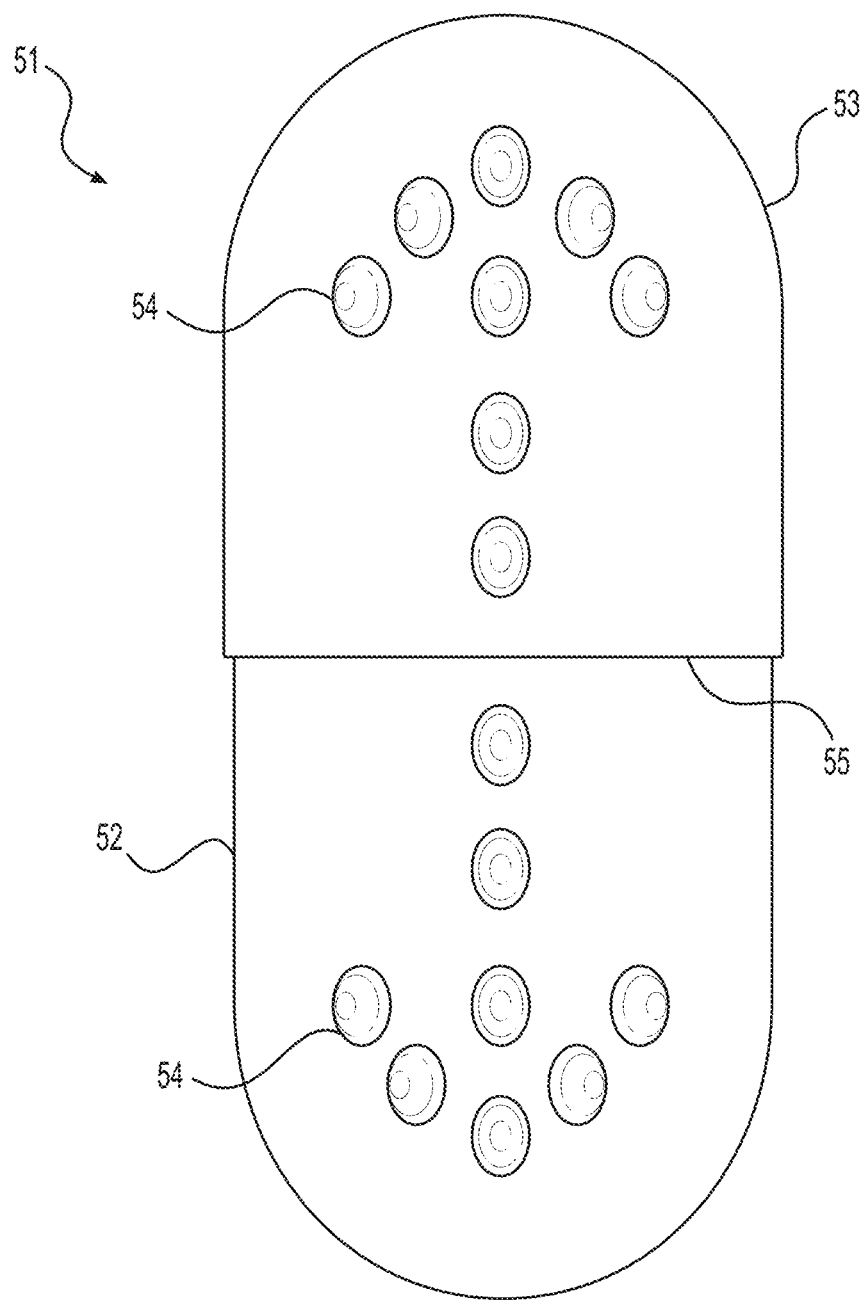
FIG. 5 is a schematic illustration of a capsule according to an embodiment of the disclosure.
Figure 6:
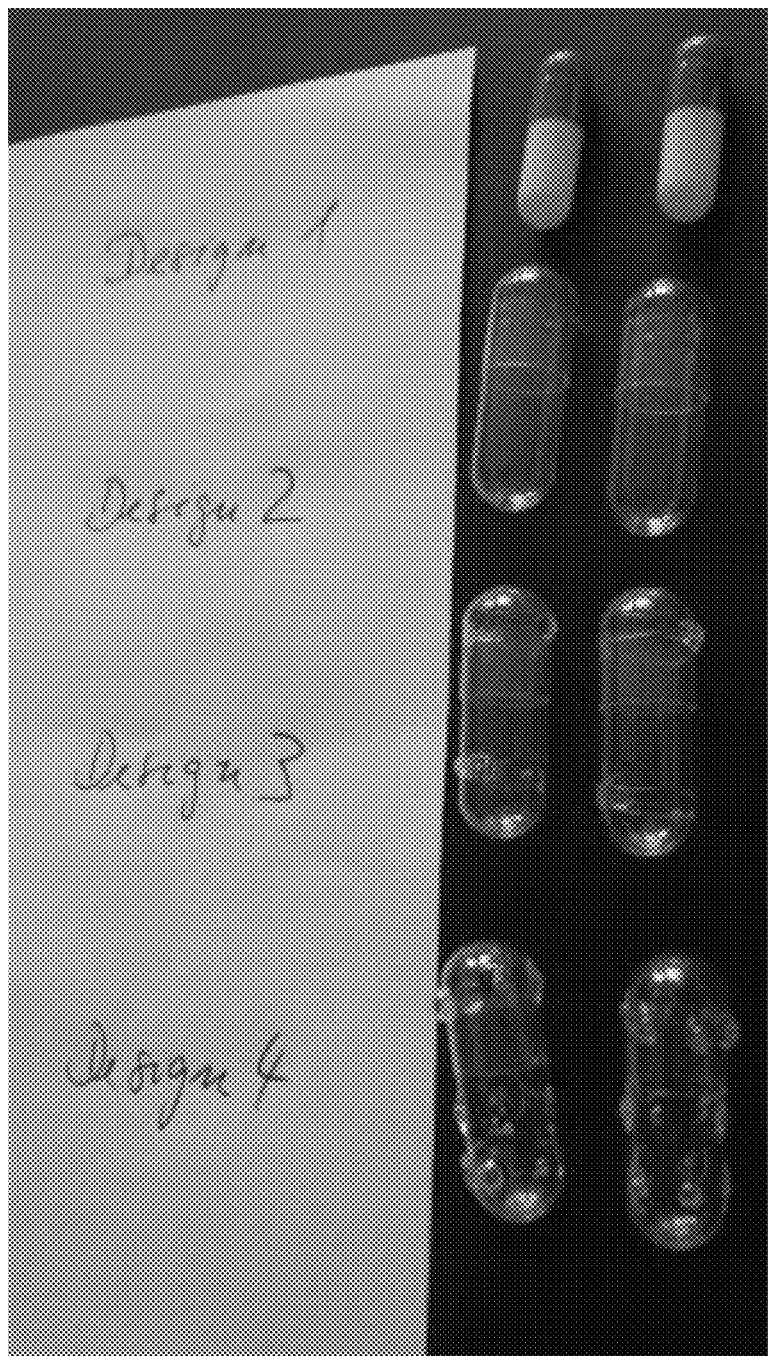
FIG. 6 is a photograph of exemplary samples.

In an embodiment, the one or more protrusions may form a pattern on the surface of the capsule (as exemplified in FIGS. 4 and 5). Typically the pattern may be arranged to indicate the direction of opening of the capsule or provide a message (such as in the form of a braille) that the capsule is not for ingestion but rather for opening the contents over a food product.

In an embodiment, the distance d is from 50 μm to 2000 μm, preferably from 100 μm to 1000 μm, more preferably from 150 μm to 700 μm. Distances below the identified lower limit are too small to provide a sufficiently strong tactile perception when handled by users with average sized fingers or fail to provide sufficient grip, on the other hand distances above the identified upper limit are too large to sufficient surface area increase for improved grip and provide a limited perception of non-suitability to swallowing.

In an embodiment, the protrusion(s) has a height that extends along an axis perpendicular to the capsule centerline X (i.e., extends from an outer surface of the capsule in a direction opposite to an inner or internal surface of the capsule), said height typically being from 300 μm to 2000 μm, preferably from 500 μm to 1500 μm, more preferably from 700 μm to 1200 μm, even more preferably from 800 μm to 1000 μm. Heights below the lower limit do not provide sufficient gripping surface and/or visual discrimination, whilst heights above the upper limit may reduce the overall finger contact area by not allowing a portion of the fingers to easily come into contact with both the capsule outer surface as well as the protrusion(s).

When the protrusions are in the form of one or more rings (whether continuous or discontinuous), the rings are substantially equidistant from each other.

In a preferred embodiment, the protrusions are substantially curvilinear (i.e., non-sharp) in shape. Advantages of a curved protrusion profile include to increase the overall surface area of contact as well as providing a more comfortable gripping surface for ease of capsule opening.

The protrusion(s) may be formed by banding, 3D-printing, ink printing, applying of adhesive labels or the like, as will be described in more detail in the following passages. A highly suitable and preferred process is the banding process due to its reduced cost and production speed capabilities, although it would be apparent to a person skilled in the art that other processes could be used as long as capable of providing the desired protruding feature characteristics described herein.

In an embodiment, the sensory trigger 4, 24, 34, 44, 54 comprises one or more friction inducing members arranged to provide a gripping surface to ease opening of said capsule compared to a capsule free of said friction inducing members. The friction inducing members may be in the form of one or more protrusions as described above typically made of a suitable material to increase the gripping friction when handled with fingers by a subject.

In an embodiment, the sensory trigger 4, 24, 34, 44, 54 comprises a visual warning to a subject not to ingest said capsule, typically in the form of a print over at least the cap and/or body outer surface. The print may be in the form of an aqueous based ink comprising the taste imparting materials and/or abrasive particles described below, as well as one or more coloring agents.

The sensory trigger may be of a different color to the color of the cap and/or body of the capsule, An advantage of such arrangement is to provide additional visual distinction of the sensory trigger versus the capsule surfaces.

In one embodiment, the sensory trigger 4, 24, 34, 44, 54 comprises one or more effervescent materials arranged to provide a fizzing sound when in contact with water and/or a mucosal surface of a subject.

Suitable effervescent materials for use herein comprise a combination of one or more acid components (typically selected from the group consisting of citric acid, malic acid, tartaric acid, adipic acid, fumaric acid, and mixtures thereof), and one or more carbonate components (typically selected from the group consisting of sodium bicarbonate, potassium bicarbonate, sodium carbonate, potassium carbonate, and mixtures thereof).

In an embodiment, the sensory trigger 4, 24, 34, 44, 54 is formed by one or more bands of a banding composition along at least a portion of the cap 3, 23, 33, 43, 53 and/or body 2, 22, 32, 42, 52 circumference and over the outer surface of said cap 3, 23, 33, 43, 53 and/or body 2, 22, 32, 42, 52, said one or more bands being acentrically located at a position distal from a cap rim 5, 25, 35, 45, 55 such that the cap 3, 23, 33, 43, 53 and body 2, 22, 32, 42, 52 are not joined together by said band. The bands may form one or more protrusions as described above, and can be applied using any suitable capsule banding process and equipment such as described in e.g., F. Podczeck and B. Jones, *Pharmaceutical Capsules*, 2$^{nd}$ Ed., Pharmaceutical Press (2004), pp. 182-183, with the exception that instead of applying the band on the rim of the capsule, the one or more bands are applied accentrically on the cap and/or body such that sealing of the cap to the body is rather avoided.

Preferably, the one or more bands are applied to said capsule in the form of a liquid banding composition that is subsequently dried and solidified. The liquid banding composition may be an aqueous composition comprising one or more bio-adhesive polymers, optional plasticizers, and optional taste imparting materials.

The bio-adhesive polymers in particular are arranged to provide additional stickiness when in contact with internal (like tongue or other tissues in the mouth) or external (like skin, particularly of the fingers) mucosal surfaces of a subject. An advantage is not only to improve gripping for opening of the capsule but further added disincentive for swallowing due to the sticky feeling/signal provided.

The liquid banding composition may further comprise a plurality of abrasive particles arranged to increase the surface roughness of the bands, preferably wherein the abrasive particles have an average diameter of from 300 µm to 1500 µm, preferably from 500 µm to 1200 µm, more preferably from 700 µm to 1000 µm, even more preferably from 750 µm to 900 µm. The abrasive particles may be comprised at a level of from 5% to 20%, preferably 8% to 15%, by weight of the total banding composition.

The bio-adhesive polymers herein may be comprised at a total level of from 2% to 30%, preferably from 5% to 28%, preferably from 10% to 25%, preferably from 11% to 20%, even more preferably from 12% to 15%, by weight of the total banding composition.

Suitable bio-adhesive polymers are typically selected from the group consisting of hydroxypropylmethylcellulose (HPMC), methylcellulose (MC), sodium alginate (SA), carrageenan (CA) and metolose (MET), chitosan; polyacrylates (Carbopols), carboxymethylcelluloses (CMC); Hydroxyethyl cellulose (HEC); Carragenan; Polyethylenoxide (PEO); Polycarbophil polymers; anionic and cationic thiolated polymers like polycarbophil-cysteine, poly(acrylic acid)-cysteine, alginate-cysteine, chitosan-4-thio-butylamidine, chitosan-thioglycolic acid, and chitosan-2-mercaptoethylamine, chitosan-thioglycolic acid mercaptonicotin amide, pectin-cysteine-mercaptonicotinic acid and chitosan-4-thiobutylamidine-mercaptonicotinamide, Poly(acrylic acid)-homocysteine, Chitosan-iminothiolane; Lectins; hyaluronic acid, xanthan gum, locust bean gum, guar gum; polyphosphazenes, gelatin, and mixtures thereof. Preferred bio-adhesive polymers are selected from the group consisting of hydroxypropylmethylcellulose (HPMC), methylcellulose (MC), sodium alginate (SA), polyvinylpyrrolidone (PVP), polyvinyl alcohol) (PVA), and mixtures thereof.

The plasticizers herein may be comprised at a total level of from 0% to 20%, preferably from 3% to 15%, preferably from 5% to 10%, by weight of the total banding composition.

Suitable plasticizers are typically selected from the group consisting of Glycerol, propylene glycol, low molecular weight polyethylene glycols, phthalate derivatives like dimethyl, diethyl and dibutyl phthalate, citrate derivatives such as tributyl, triethyl, acetyl citrate, triacetin, castor oil, and mixtures thereof.

The taste imparting materials herein may be comprised at a total level of from 0% to 5%, preferably from 0.01% to 2%, preferably from 0.05% to 1%, more preferably from 0.1% to 0.5%, by weight of the total banding composition.

Suitable taste imparting materials herein are preferably plant derived and may be selected from the group consisting of Secoiridoid derivative like foliamenthin, menthiafolin, dihydrofoliamenthin, centapikrosid and gentiopikrosid derivatives (e.g., amarogentin, swerosid, gentiobiose); iridoide derivatives (e.g., loganin, harpagosid); kondurangenin derivatives; chinin, chinidin, cinchoninchinova acid, diterpene link marrubiin, sesquiterpenlactones (e.g., nobilin, salonitenolid, cnicin, taraxin acid and derivative (e.g., taraxocolids), cynaropikrin, quassin and quassin derivatives, acorons, ajmalin, atropin, hyoscyamin, scopolamin, aloe, berberin, carnosol, cascarillin, cucurbitacine, columbin, gentianose, ginkgolide, humulone, lingane,lupulone,lycopodin, naringin, hesperidin, hesperidose, quillajasaponin, saponines, saponosides, fenchon, absinthin, and mixtures thereof.

In another embodiment, the one or more bands are applied to said capsule in the form of adhesive strips (or adhesive labels) adhered to said cap and/or body outer surface. The adhesive strips may be comprised of the same one or more bio-adhesive polymers, optional plasticizers, optional abrasive particles, and optional taste imparting materials described above. The backside of the adhesive strip/label may comprise a glue or other similar adhesive substance that is capable of adhering to the capsule surface upon drying.

In an embodiment, the capsule is dimensioned such that the length thereof along an axis parallel to the capsule centerline X, when in a fully assembled and closed state, is of from 25 to 30 mm, and said capsule 1, 21, 31, 41, 51 further having a maximum diameter of from 9 to 11 mm, and wherein the body 2, 22, 32, 42, 52 of said capsule 1, 21, 31, 41, 51 is elongated such that the length ratio Lb:Lc of an exposed body surface Lb (i.e., the part not covered by the cap) and the cap Lc along the capsule centerline X is from 1 to 1.3, more preferably greater than 1, even more preferably from 1.1 to 1.3. An advantage of this embodiment is that the sensory trigger is provided by the dimensional characteristics as described which allow to achieve added deterrence to ingestion due to the particular larger size that makes it difficult to swallow.

In a preferred embodiment, the sensory trigger 4, 24, 34, 44, 54 comprises one or more taste inducing materials to impart a taste to the capsule, said taste being selected from salty, bitter, sour, acrid or combinations thereof. Typically the one or more taste inducing materials for use herein are as described above as "taste imparting materials", and preferably selected from the group consisting of Secoiridoid derivative like foliamenthin, menthiafolin, dihydrofoliamenthin, centapikrosid and gentiopikrosid derivatives (e.g., amarogentin, swerosid, gentiobiose); iridoide derivatives (e.g., loganin, harpagosid); kondurangenin derivatives; chinin, chinidin, cinchoninchinova acid, diterpene link marrubiin, sesquiterpenlactones (e.g., nobilin, salonitenolid, cnicin, taraxin acid and derivative (e.g., taraxocolids), cynaropikrin, quassin and quassin derivatives, acorons, ajmalin, atropin, hyoscyamin, scopolamin, aloe, berberin, carnosol, cascarillin, cucurbitacine, columbin, gentianose, ginkgolide, humulone, lingane, lupulone, lycopodia, naringin, hesperidin, hesperidose, quillajasaponin, saponines, saponosides, fenchon, absinthin, and mixtures thereof. Preferably selected from the group consisting of foliamenthin, menthiafolin, dihydrofoliamenthin, amarogentin, swerosid, gentiobiose, loganin, harpagosid, nobilin, salonitenolid, cnicin, taraxin acid, taraxocolids, cynaropikrin, quassin and quassin derivatives, acorons, ajmalin, atropin, hyoscyamin, scopolamin, aloe, berberin, camosol, cascarillin, cucurbitacine, columbin, gentianose, ginkgolide, humulone, lingane, lupulone, lycopodia, naringin, hesperidin, hesperidose, quillajasaponin, saponines, saponosides, fenchon, absinthin, and mixtures thereof. Other suitable examples include materials like denatonium benzoate (commercially available under the names of BITTERANT-b, BITTER+PLUS, Bitrex or Aversion).

In a preferred embodiment, the composition of the sensory trigger 4, 24, 34, 44, 54 is different from the composition of the capsule cap and body shells. An advantage of this arrangement is to provide unique and enhanced deterrence and grip than if the same capsule material was used, as well as a more differentiated feel to the touch.

In a preferred embodiment, the sensory trigger 4, 24, 34, 44, 54 is distinct and fixedly joined to said capsule. An advantage of this arrangement is that is enables improved flexibility in designing and applying the sensory trigger without being constricted to hard capsule making process parameters, equipment, and limitations.

In an embodiment, the capsule shells are made of the same or different materials, preferably the same materials. The material may comprise any material known in the art for making hard capsules such as gelatin (bovine, porcine or fish source), polymers (such as cellulose derivatives, polysaccharides, polyacrylates and the like). Preferably however, the material comprises one or more acid resistant and/or enteric materials, typically selected from the group consisting of hydroxypropyl methylcellulose (HPMC), cellulose acetate phthalate (CAP), hydroxypropyl methylcellulose acetate succinate (HPMCAS), and mixtures thereof.

In an embodiment, the capsules are selected from HPMC-based capsules (such as Vcaps® or Vcaps Plus® capsules supplied by CAPSUGEL®), pullulan-based capsules (such as Plantcaps® capsules supplied by CAPSUGEL®), HPMC/Gellan-based capsules (such as DRcaps® capsules supplied by CAPSUGEL®), gelatin-based capsules (such as Coni-Snap® capsules supplied by CAPSUGEL®).

In an embodiment, the capsule further comprises one or more locking features arranged to provide pre-locking and fully-locking forces, wherein the pre-locking force is less than the fully-locking force and the fully-locking force is of from 0.29 N to 1.96 N, preferably from 0.49 N to 1.47 N, more preferably from 0.98 N to 1.47 N. Suitable locking features are described in EP2994114A1 and are typically in the form of one or more locking ring recesses on the outer body surface and a plurality of discrete inner cap inwardly protruding dimples for engagement with said recesses. An advantage of this arrangement is to provide a sufficient locking force for preventing accidental opening of the capsule, for example during transportation and handling, but at the same time provide easy opening thereof for administration of the contents.

Drug/Medicament

Drugs (i.e., medicaments) suitable for use in the dosage form articles described herein may take any form and be for any treatment of a human or animal subject. This includes not only pharmaceutical compounds but also dietary supplements such as vitamins, minerals and the like.

The drug may be in a state selected from solid or liquid, preferably solid, at room temperature and atmospheric pressure, and comprises one or more active compounds. Its intended application is for sprinkling or pouring onto a food product prior to ingestion thereof by a subject, or for pouring in feeding tubes for administration to subjects.

The medicament may be solid and in the form of spray dried dispersions, pellets, granules and the like.

Suitable compounds (and generally encompassed by the term "medicament" as used herein) for delivery according to the disclosure include, but are not limited to, particulate, powder, waxy, liquid, and/or pellet forms of the following:

a) pharmaceuticals (also called pharmaceutical actives) such as betamethasone, thioctic acid, sotalol, salbutamol, norfenefrine, silymahn, dihydroergotamine, buflomedil, etofibrate, indomethacin, oxazepam, acetyldigitoxins, piroxicam, halopehdol, isosorbide mononitrate, amithptyline, diclofenac, nifedipine, verapamil, pyritinol, nitrendipine, doxy-cycline, bromhexine, methylprednisolone, clonidine, fenofibrate, allopurinol, pirenzepine, levothyroxine, tamoxifen, metildigoxin, o-(B-hydroxyethyl)-rutoside, propicillin, aciclovir-mononitrate, paracetamolol, naftidrofuryl, pentoxifylline, propafenone, acebutolol, 1-thyroxin, tramadol, bromocriptine, loperamide, ketofinen, fenoterol, ca-dobesilate, propranolol, minocycline, nicergoline, ambroxol, metoprolol, B-sitosterin, enalaprilhydrogenmaleate, bezafibrate, isosorbide dinitrate, gallopamil, xantinolnicotinate, digitoxin, flunitrazepam, bencyclane, depanthenol, pindolol, lorazepam, diltiazem, piracetam, phenoxymethylpenicillin, furosemide, bromazepam, flunarizine, erythromycin, metoclo-pramide, acemetacin, ranitidine, biperiden, metamizol, doxepin, dipotassiumichloraze-pat, tetrazeparn, estramustinephosphate, terbutaline, captopril, maprotiline, prazosin, atenolol, glibenclamid, cefaclor, etilefrin, cimetidine, theophylline, hydromorphone, ibu-profen, primidone, clobazam, oxaceprol, medroxyprogesterone, flecainide, Mg-pyhdoxal-5-phosphateglutaminate, hymechromone, etofyllineclofibrate, vincamine, cin-narizine, diazepam, ketoprofen, flupentixol, molsidomine, glibornuhde, dimethindene, melperone, soquinolol, dihydrocodeine, clomethiazole, clemastine, glisoxepid, kallidino-genase, oxyfedhne, baclofen, carboxymethylcystsin, thioredoxin, betahistine, 1-tryptophan, myrtol, bromelain, prenylamine, salazosulfapyridine, astemizole, sulpiride, benzerazid, dibenzepin, acetylsalicylic acid, miconazole, nystatin, ketoconazole, sodium picosulfate, colestyramate, gemfibrozil, rifampin, fluocortolone, mexiletine, amoxicillin, terfenadine, mucopolysaccharidpolysulfuric acid, triazolam, mianserin, tiaprofensaure, ameziniummethylsulfate, mefloquine, probucol, quinidine, carbamazepine, Mg-1-aspartate, penbutolol, piretanide, amitriptyline, caproteron, sodium valproinate, me-beverine, bisacodyl, 5-amino-salicyclic acid, dihydralazine, magaldrate, phenprocou-mon, amantadine, naproxen, carteolol, famotidine, methyldopa, auranofins, estriol, nadolol, levomepromazine, doxorubicin, medofenoxat, azathioprine, flutamide, norfloxacin, fendiline, prajmaliumbitartrate, aescin acromycin, anipamil, benzocaine, [beta]-carotene, cloramphenicol, chlorodiazepoxid, chlormadinoneacetate, chlorothiazide, cin-narizine, clonazepam, codeine, dexamethasone, dicumarol, digoxin, drotaverine, grami-cidine, griseofulvin, hexobarbital hydrochlorothiazide, hydrocortisone, hydroflumethiazide, ketoprofen, lonetil, medazepam, mefruside, methandrostenolone, sulfaperine, nalidixic acid, nitrazepam, nitrofurantoin, estradiol, papaverine, phenacetin, phenobarbi-tal, phenylbutazone, phenytoin, prednisone, reserpine, spironolactine, streptomycin, sul-famethizole, sulfamethazine, sulfamethoxazole, sulfamethoxydiazinon, sulfathiazole, sulfisoxazole, testosterone, tolazamide, tolbutamide, trimethoprim, tyrothricin, antacids, reflux suppressants, antiflatulents, antidopaminergics, proton pump inhibitors, H2-receptor antagonists, cytoprotectants, prostaglandin analogues, laxatives, antispasmodics, antidiarrhoeals, bile acid sequestrants, opioids, beta-receptor blockers, calcium channel blockers, diuretics, cardiac glycosides, antiarrhythmics, nitrates, antianginals, vasoconstrictors, vasodilators, ACE inhibitors, angiotensin receptor blockers, alpha blockers, anticoagulants, heparin, antiplatelet drugs, fibrinolytic, anti-hemophilic factor, haemostatic drugs, hypolipidaemic agents, statins, hypnotics, anaesthetics, antipsychotics, antidepressants (including tricyclic antidepressants, monoamine oxidase inhibitors, lithium salts, selective serotonin reuptake inhibitors), antiemetics, anticonvulsants, an-tiepileptics, anxiolytics, barbiturates, movement disorder drugs, stimulants (including amphetamines), benzodiazepine, cyclopyrrolone, dopamine antagonists, antihistamines, cholinergics, anticholinergics, emetics, cannabinoids, 5-HT antagonists, analgesics, muscle relaxants, antibiotics, sulfa drugs, aminoglycosides, fluoroquinolones, bronchodilators, NSAIDs, anti-allergy drugs, antitussives, mucolytics, decongestants, corticosteroids, beta-receptor antagonists, anticholinergics, steroids, androgens, antian-drogens, gonadotropin, corticosteroids, growth hormones, insulin, antidiabetic drugs (including sulfonylurea, biguanide/metformin, and thiazolidinedione), thyroid hormones, antithyroid drugs, calcitonin, diphosponate, vasopressin analogs, contraceptives, follicle stimulating hormone, luteinising hormone, gonadotropin release inhibitor, progestogen, dopamine agonists, oestrogen, prostaglandin, gonadorelin, clomiphene, tamoxifen, di-ethylsti I bestrol, antimalarials, anthelmintics, amoebicides, antivirals, antiprotozoals, vaccines, immunoglobulin, immunosuppressants, interferon, monoclonal antibodies, and mixtures thereof;

b) vitamins, e.g., fat-soluble vitamins such as vitamins A, D, E, and K, and water soluble vitamins such as vitamin C, biotin, folate, niacin, pantothenic acid, riboflavin, thiamin, vitamin B6, vitamin B12, and mixtures thereof;

c) minerals, such as calcium, chromium, copper, fluoride, iodine, iron, magnesium, manganese, molybdenum, phosphorus, potassium, selenium, sodium (including sodium chloride), zinc, and mixtures thereof;

d) dietary supplements such as herbs or other botanicals, amino acids, and substances such as enzymes, organ tissues, glandulars, and metabolites, as well as concentrates, metabolites, constituents, extracts of dietary ingredients, oils such as krill oil and mixtures thereof;

e) homoeopathic ingredients such as those listed in the Homeopathic Pharmacopoeia of the United States Revision Service (HPRS) and mixtures thereof. It must be recognized, of course, that the HPRS is periodically updated and that the present invention includes homeopathic ingredients that may be added to the HPRS;

f) probiotics and yeast, such as bacteria selected from the group consisting of Lactobacillus (Döderlein's bacilli) such as *Lactobacillus crispatus, Lactobacillus jensinii, Lactobacillus johnsonii, Lactobacillus gasseri, Enterococcus faecium,* or fungi selected from the group of Saccharomycetales such as *Saccharomyces boulardii.* g) hormones, such as estrogen (i.e., a natural estrogen or a synthetic compound that mimics the physiological effect of natural estrogens) including, without limitation, estradiol (17-estradiol), estridiol acetate, estradiol benzoate, estridiol cypionate, estridiol decanoate, estradiol diacetate, estradiol heptanoate, estradiol valerate, 17a-estradiol, estriol, estriol succinate, estrone, estrone acetate, estrone sulfate, estropipate (piperazine estrone sulfate), ethynylestradiol (17a-ethynylestradiol, ethinylestradiol, ethinyl estradiol, ethynyl estradiol), ethynylestradiol 3-acetate, ethynylestradiol 3-benzoate, mestranol, quinestrol, nitrated estrogen derivatives or combinations thereof; or progestin (i.e., natural or synthetic compounds that possesses progestational activity including, without limitation, nortestosterone, ethynyltestosterone, deacetylnorgestimate, hydroxyprogesterone, 19-norprogesterone, 3P-hydroxydesogestrel, 3-ketodesogestrel (etonogestrel), acetoxypregnenolone, algestone acetophenide, allylestrenol, amgestone, anagestone acetate, chlormadinone, chlormadinone acetate, cyproterone, cyproterone acetate, dernegestone, desogestrel, dienogest, dihydrogesterone, dimethisterone, drospirenone, dydrogesterone, ethisterone (pregneninolone, 17a-ethynyltestosterone), ethynodiol diacetate, fluorogestone acetate, gestrinone, gestodene, gestodene, gestonorone, gestrinone, hydroxymethylprogesterone, hydroxymethylprogesterone acetate, hydroxyprogesterone, hydroxyprogesterone acetate, hydroxyprogesterone caproate, levonorgestrel (1-norgestrel), lynestrenol (lynoestrenol), mecirogestone, medrogestone, medroxyprogesterone, medroxyprogesterone acetate, megestrol, megestrol acetate, melengestrol, melengestrol acetate, nestorone, nomegestrol, norelgestromin, norethindrone (norethisterone) (19-nor-17a-ethynyltestosterone), norethindrone acetate (norethisterone acetate), norethynodrel, norgestimate, norgestrel (d-norgestrel and dl-norgestrel), norgestrienone, normethisterone, progesterone, promegestone, quingestanol, tanaproget, tibolone, trimegestone, or combinations thereof.

and mixtures in any combination of the foregoing.

Methods and Uses

A preferred method of making a capsule as described herein comprises the steps of:

providing a capsule body 2, 22, 32, 42, 52 and cap 3, 23, 33, 43, 53;

telescopically joining the body 2, 22, 32, 42, 52 and cap 3, 23, 33, 43, 53 to form a hard capsule:

applying a sensory trigger 4, 24, 34, 44, 54 over at least a portion of the outer surface of said capsule, said sensory trigger 4, 24, 34, 44, 54 arranged to provide a visual, taste, and/or tactile deterrence to ingestion of said hard capsule.

In an embodiment, the method comprises the step of accentrically banding the sensory trigger 4, 24, 34, 44, 54 to the capsule, such that the cap and body are not joined by the resulting one or more bands, preferably by banding a portion of the cap and body shell outer surface with a banding composition, said portion typically not including and being distal from a seam of the capsule.

In an alternative embodiment, the method comprises the step of accentrically applying the sensory trigger 4, 24, 34, 44, 54 in the form of one or more adhesive labels to the capsule, such that the cap and body are not joined by the one or more adhesive labels, preferably by applying said sensory trigger to a portion of the cap and body shell outer surface, said portion typically not including and being distal from a seam of the capsule.

In an embodiment, the band or adhesive label is applied more than once over the capsule. An advantage of this arrangement is to form protrusions of sufficient depth to not only provide the visual and tactile deterrence to ingestion but further increase the surface area for better grip and ease of opening of the capsule.

EXAMPLES

Example 1

Table 1 illustrates exemplary banding solutions with hydroxylpropyl methyl cellulose (HPMC), methyl cellulose (MC), or hydroxyl ethyl cellulose (HEC) respectively as muco-adhesive (or bio-adhesive) polymer. The appropriate quantity by weight of polymer powder is first dispersed in demineralized-water at room temperature under stirring to obtain the desired weight ratio. Where appropriate, the indicated amount of surfactant (sorbitan monolaureate) and ammonia solution is added to the dispersion progressively under gentle stirring until the polymer particles are totally dissolved. A colorant can be added, like 0.1% solution of Patent Blue V—C.I. Food Blue 5 E131 (based on the polymer weight), to aid in the visualization of the banding.

Banding is performed on a lab scale banding equipment from S1 Bench-Top Capsule Band-Sealer (Qualicaps) or MG2 (Model SL/M) with drying under room temperature conditions. The banding is applied to Coni-Snap® capsules (supplied by Capsugel®). The capsules are accentrically banded such that the seam of the capsule remains free of banding solution and the cap and body of the capsule are not joined by the band.

TABLE 1

| Chemical name | Concentration (%, w/w) | Ethanol (%, w/w) | Water (%, w/w) | NH$_3$ (35%) (%, w/w) | Sorbitan monolaureate (%, w/w) |
|---|---|---|---|---|---|
| HPMC | 24 | 37.988 | 37.988 | — | 0.024 |
| MC | 23.3 | 38 | 38 | 0.7 | — |
| HEC | 24 | 38 | 38 | — | — |

Example 2

In this example, the benefit of capsules according to an aspect of the present disclosure are compared with those of prior art capsules.

A consumer test is carried out on the following capsules (illustrated in FIG. 1): Comparative A (or Design 1); Comparative B (or Design 2); Example C (or Design 3); and Example D (or Design 4).

Comparative A is a commercially available capsule sold under the Coni-Snap® Sprinkle trade name by Capsugel. The capsule is made according to the disclosure of EP2994114A1.

Comparative B is an HPMC capsule (transparent) with increased size, size 000.

Example C is the same capsule of Comparative B, but with the further addition of two bands (one on each cap and body of the capsule). The bands are applied using standard banding equipment like the S1 Bench-Top Capsule Band-Sealer (Qualicaps) or MG2 (Model SL/M) with drying under room temperature conditions. The band forming two protrusions over the capsule surface in the form of continuous rings along the circumference thereof.

Example D is the same capsule of Comparative C, but with the addition of bands in the form of a plurality of protrusions, in series, forming discontinuous rings along the circumference of the capsule surface.

Each capsule (of Design 1-4) is presented to a panel of 17 people (n=17) of a representative distribution of different ages and sex. Each member of the panel is requested to answer a questionnaire, and the results are reported in the tables that follow.

TABLE 2

How likely it is that you would swallow the capsule?

| | not likely | less likely | somewhat likely | likely | very likely |
|---|---|---|---|---|---|
| Design 1 | 0 | 0 | 0 | 1 | 16 |
| Design 2 | 0 | 0 | 10 | 5 | 2 |
| Design 3 | 9 | 6 | 2 | 0 | 0 |
| Design 4 | 12 | 5 | 0 | 0 | 0 |

TABLE 3

Which capsule provides the best grip?

| | poor | less suited | somewhat suited | good | best suited |
|---|---|---|---|---|---|
| Design 1 | 14 | 3 | 0 | 0 | 0 |
| Design 2 | 8 | 7 | 2 | 0 | 0 |
| Design 3 | 0 | 1 | 3 | 9 | 4 |
| Design 4 | 0 | 0 | 4 | 7 | 9 |

TABLE 4

What do you find easier to open/handle?

| | poor | less suited | somewhat suited | good | best suited |
|---|---|---|---|---|---|
| Design 1 | 2 | 15 | 0 | 0 | 0 |
| Design 2 | 1 | 10 | 6 | 0 | 0 |
| Design 3 | 0 | 0 | 5 | 11 | 1 |
| Design 4 | 0 | 0 | 4 | 10 | 3 |

TABLE 5

On an overall scale, what capsule would you prefer for opening?

| | not preferred | less preferred | somewhat preferred | preferred | most preferred |
|---|---|---|---|---|---|
| Design 1 | 13 | 4 | 0 | 0 | 0 |
| Design 2 | 0 | 10 | 6 | 1 | 0 |
| Design 3 | 0 | 2 | 2 | 7 | 6 |
| Design 4 | 0 | 0 | 1 | 5 | 11 |

The results indicate that Designs 3 and 4 (Examples C and D) perform significantly better not only in terms of deterrence to swallowing but also for ease of opening.

The dimensions and values disclosed herein are not to be understood as being strictly limited to the exact numerical values recited. instead, unless otherwise specified, each such dimension is intended to mean both the recited value and a functionally equivalent range surrounding that value. For example, a dimension disclosed as "40 mm" is intended to mean "about 40 mm" (i.e., every value in a practical range close to 40 mm).

The invention claimed is:

1. A hard capsule for sprinkle applications comprising at least one body and at least one cap telescopically engageable with the body wherein the cap and the body are separable to allow dispensing of comestible contents therefrom, wherein the capsule is designed to deter ingestion by comprising a sensory trigger over at least a portion of an outer surface of the capsule, wherein the sensory trigger is a deterrence to ingestion of the hard capsule and comprises one or more taste inducing materials to impart a taste to the capsule, the taste being salty, bitter, sour, acrid and/or any combination thereof.

2. A capsule according to claim 1 wherein the sensory trigger comprises at least two protrusions in the form of continuous rings along the circumference of the cap and/or body, wherein the rings are disposed substantially parallel to each other and at a distance (d) separating the rings in a direction parallel to a capsule centerline (X).

3. A capsule according to claim 1 wherein the sensory trigger comprises at least two discontinuous rings along the circumference of the cap and/or body, the rings disposed substantially parallel to each other and at a distance (d) separating the rings in a direction parallel to a capsule centerline (X), and wherein the discontinuous rings are formed by a plurality of protrusions and/or recesses arranged in series.

4. A capsule according to claim 2 wherein the distance (d) is from 50 μm to 2000 μm.

5. A capsule according to claim 1 wherein the sensory trigger is formed by one or more bands of a banding composition along at least a portion of the cap and/or body circumference and over the outer surface of the cap and/or body, the one or more bands being acentrically located at a position distal from a cap rim such that the cap and body are not joined together by the band.

6. A capsule according to claim 2 wherein the distance (d) is from 150 μm to 700 μm.

7. A capsule according to claim 5 wherein the one or more bands are adhesive strips adhered to the cap and/or body outer surface.

8. A capsule according to claim 2 wherein a length thereof along an axis parallel to the capsule centerline (X), when in a fully assembled and closed state, is from 25 mm to 30 mm, and the capsule further having a maximum diameter of from 9 mm to 11 mm, and wherein the body of the capsule is elongated such that the length ratio (Lb:Lc) of an exposed body surface (Lb) and the cap (Lc) along the capsule centerline (X) is from 1 to 1.3.

9. A capsule according to claim 1 wherein the one or more taste inducing materials are a secoiridoid derivative, a gentiopikrosid derivative, a iridoide derivative, a kondurangenin derivative, chinin, chinidin, cinchoninchinova acid, a diterpene, a sesquiterpenlactone, a taraxin acid, a taraxin acid derivative, cynaropikrin, quassin, a quassin derivative, an acoron, ajmalin, atropine, hyoscyamin, scopolamine, aloe, berberin, carnosol, cascarillin, cucurbitacine, columbin, gentianose, ginkgolide, humulone, lingane, lupulone, lycopodin, naringin, hesperidin, hesperidose, quillajasaponin, saponines, saponosides, fenchon, absinthin, or any mixture thereof.

10. A capsule according to claim 1 wherein the composition of the sensory trigger is different from the composition of the capsule cap and body shells.

11. A capsule according to claim 1 wherein the sensory trigger is distinct and fixedly joined to the capsule.

12. A method of making a capsule comprising:
providing a capsule body and cap according to claim 1;
telescopically joining the body and cap to form a hard capsule;
applying a sensory trigger over at least a portion of the outer surface of the capsule, the sensory trigger arranged to provide a visual, taste, and/or tactile, deterrence to ingestion of the hard capsule such that the hard capsule is not ingested.

13. A capsule according to claim 3 wherein the distance (d) is from from 150 μm to 700 μm.

14. A capsule according to claim 3 wherein the rings are substantially equidistant from each other.

15. A capsule according to claim 3 wherein a length thereof along an axis parallel to the capsule centerline (X), when in a fully assembled and closed state, is from 25 mm to 30 mm, and the capsule further having a maximum diameter of from 9 mm to 11 mm, and wherein the body of the capsule is elongated such that the length ratio (Lb:Lc) of an exposed body surface (Lb) and the cap (Lc) along the capsule centerline (X) is from 1 to 1.3.

16. A capsule according to claim 2 wherein the composition of the sensory trigger is different from the composition of the capsule cap and body shells.

* * * * *